United States Patent [19]

Pawlowski

[11] Patent Number: 4,760,006

[45] Date of Patent: Jul. 26, 1988

[54] 2,3-BIS(DIALKYLAMINOPHENYL)QUINOXALINES AND THEIR USE IN ELECTROPHOTOGRAPHIC RECORDING MATERIALS

[75] Inventor: Georg Pawlowski, Wiesbaden, Fed. Rep. of Germany

[73] Assignee: Hoechst Aktiengesellschaft, Fed. Rep. of Germany

[21] Appl. No.: 739,024

[22] Filed: May 29, 1985

[30] Foreign Application Priority Data

May 29, 1984 [DE] Fed. Rep. of Germany ....... 3420039

[51] Int. Cl.$^4$ ................. C07D 241/42; G03G 5/09; G03G 5/06
[52] U.S. Cl. ................................. 430/78; 544/353; 430/49; 430/69; 430/31
[58] Field of Search .................. 544/353; 430/78, 31, 430/49, 69

[56] References Cited

U.S. PATENT DOCUMENTS 3,765,898 10/1973 Bauer et al. ........................... 96/115
4,125,725 11/1978 Duffy .................................. 544/353
4,628,020 12/1986 Stahlhofen ........................... 430/165

FOREIGN PATENT DOCUMENTS 599569 5/1978 Switzerland .
1004461 9/1965 United Kingdom .
1062935 3/1967 United Kingdom .

OTHER PUBLICATIONS

Roubinek, Chemical Abstract, vol. 101, 38427m (1984).
Kraska, Chemical Abstract, vol. 90 56315 g (1978).
Gerlicz, Chemical Abstract, vol. 87, 137307 w 1976).
Gerlicz, Chemical Abstract, vol. 87, 152269d (1977).
Jarrar, Chemical Abstract, vol. 89, 24276h (1978).
A. H. C., Chemical Abstract, vol. 85, 169706a (1975).
Solodoua, Chemical Abstract, vol. 96, 199729e (1981).
Tuzan et al., "4,4'-Bis(dimethylamino)benzil . . . ", Organic Syntheses, vol. 41, pp. 1–4.
Ehrlich et al., "Experiments in the Veratrole and Quinozaline Groups", J. Organic Chem. 12, pp. 522–534, 1974.
Bost et al., "The Preparation of Some Substituted Quinozalines", J.A.C.S. 70, pp. 903–905, 1984.

Primary Examiner—Mark L. Berch
Attorney, Agent, or Firm—Foley & Lardner, Schwartz, Jeffery, Schwaab, Mack, Blumenthal & Evans

[57] ABSTRACT

Novel 2,3-bis(dialkylaminophenyl)quinoxalines of the general formula

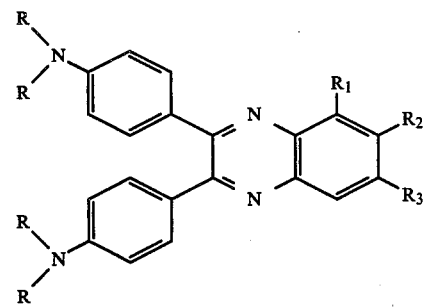

wherein
R is alkyl having up to 4 carbon atoms
$R_1$ is hydrogen or alkyl having up to 4 carbon atoms,
$R_2$ is the same as or different from $R_1$ and is selected from the group consisting of alkyl and alkoxyl having up to 4 carbon atoms, and
$R_3$ is the same as or different from $R_2$ and is selected from the group consisting of hydrogen, alkyl and alkoxyl having up to 4 carbon atoms, The compounds of the invention are useful as photoconductive substances in electrophotographic recording materials.

11 Claims, No Drawings

2,3-BIS(DIALKYLAMINOPHENYL)QUINOXALINES AND THEIR USE IN ELECTROPHOTOGRAPHIC RECORDING MATERIALS

BACKGROUND OF THE INVENTION

The present invention relates to novel 2,3,-bis(dialkylaminophenyl)quinoxalines and their use as photoconductive substances in electrophotographic recording materials, in particular for lithographic and resist applications.

It is known to use quinoxaline derivatives as photoconductors in electrophotographic recording materials (German Pat. No. 1,254,469, equivalent to British Pat. Nos. 1,062,935 and 1,004,461). The light sensitivities exhibited by the quinoxaline derivatives described therein are, however, too low to meet high-standard requirements. Due to their rather poor sensitivity, electrophotographic recording materials containing these photoconductors are, for example, not very well suited for laser exposure, since no sufficient charge contrast between the exposed and unexposed layer areas is obtained. Even when conventional light sources are used, these recording materials are found to be less suitable, for even after a prolonged, intensive exposure their residual charge is undesirably high. This is the reason why exposed layer areas accept toner material in the developing step and, as a consequence thereof, the visible image obtained exhibits low crispness and poor resolution.

It is accordingly an object of this invention to provide photoconductors for electrophotographic recording materials having a higher sensitivity to light and higher image contrast.

This object and others are achieved by a 2,3-bis(dialkylaminophenyl)quinoxaline represented by the general formula

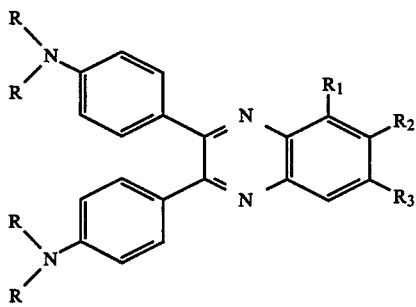

wherein R is an alkyl having up to 4 carbon atoms, $R_1$ is hydrogen or alkyl having up to a 4 carbon atoms, $R_2$ is the same as or different from $R_1$, and is selected from the group consisting of alkyl and alkoxyl having up to 4 carbon atoms, and $R_3$ is the same as or different from $R_2$ and is selected from the group consisting of hydrogen, alkyl and alkoxyl having up to 4 carbon atoms.

The objects of the invention are also achieved by a photoconductive substance useful in electrophotographic recording materials, comprising a 2,3-bis(dialkylaminophenyl)quinoxaline.

DETAILED DESCRIPTION OF THE PREFERRED EMBODIMENTS

It has surprisingly been found that highly light-sensitive electrophotographic recording materials of a low residual potential and high contrast are obtained when the photoconductive substances employed are quinoxaline derivatives which contain one or several alkyl groups or alkoxy groups in the carbocyclic ring, without other properties which are relevant for the electrophotographic process, such as discharge in the dark or printing properties, being impaired.

The present invention relates to 2,3-bis(dialkylaminophenyl)quinoxalines of the general formula

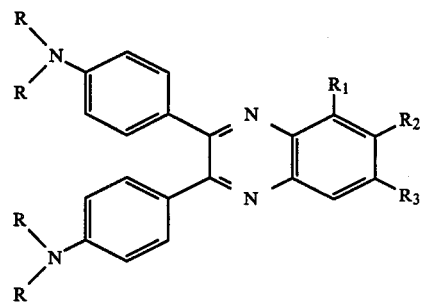

in which
R is an alkyl having up to 4 carbon atoms,
$R_1$ is hydrogen or an alkyl having up to 4 carbon atoms,
$R_2$ is the same as or different from $R_1$ and is selected from the group consisting of alkyl and alkoxyl having up to 4 carbon atoms, and
$R_3$ is the same as or different from $R_2$ and denotes hydrogen, an alkyl or an alkoxyl having up to 4 carbon atoms.

The present invention furthermore relates to the use of the 2,3-bis(dialkylaminophenyl)quinoxalines of the above formula, which have been prepared according to the invention, as photoconductive substances in electrophotographic recording materials, in particular for lithographic printing forms or resist materials, whereby it is also possible to use the quinoxaline derivatives of this invention in combination with other types of organic or inorganic photoconductors and customary additives.

Those of the 2,3-bis(dialkylaminophenyl)quinoxalines of the above general formula, in which R denotes methyl or ethyl, $R_1$ denotes hydrogen or methyl, $R_2$ denotes methyl, ethyl, methoxyl or ethoxyl, and $R_3$ denotes hydrogen, methyl or methoxyl are preferred.

Particular preference is given to those 2,3-bis(dialkylaminophenyl)quinoxalines of the above general formula, in which R denotes methyl or ethyl, $R_1$ and $R_3$ denote hydrogen or methyl and $R_2$ denotes methyl, methoxyl or ethoxyl, such as 2,3-bis(4'-dimethylaminophenyl)-6-methyl-quinoxaline, melting point (mp): 163° to 164° C.;
2,3-bis(4'-dimethylaminophenyl)-6-methoxyquinoxaline, mp: 194° to 195° C.;
2,3-bis(4'-dimethylaminophenyl)-6-ethoxy-quinoxaline, mp: 179° to 181° C.;
2,3-bis(4'-dimethylaminophenyl)-5,6-dimethylquinoxaline, mp: 212° to 213° C.;
2,3-bis(4'-dimethylaminophenyl)-6,7-dimethylquinoxaline, mp: 196° to 197° C.;
2,3-bis(4'-diethylaminophenyl)-6-methyl-quinoxaline, mp: 142° to 143.5° C.;
2,3-bis(4'-diethylaminophenyl)-6-methoxy-quinoxaline, mp: 129° to 130.5° C.;
2,3-bis(4'-diethylaminophenyl)-6-ethoxy-quinoxaline, mp: 112° to 113° C.;

2,3-bis(4'-diethylaminophenyl)-5,6-dimethylquinoxaline, mp: 142° to 143° C.;

2,3-bis(4'-diethylaminophenyl)-6,7-dimethylquinoxaline, mp: 126° to 128° C.;

The quinoxalines of this invention are novel. Their preparation is principally known. They can, for example, be prepared by reacting the corresponding bisdialkylaminobenzil with the corresponding o-phenyldiamine in a polar protic solvent, if appropriate, with the addition of an acid catalyst (see W. Bost and E. E. Towell, J. Amer. Chem. Soc., 70, 903 (1948)).

The appropriately substituted benzils, such as 4,4'-bis-dimethylaminobenzil, 4,4'-bis-diethylaminobenzil, 4,4'-bis-dipropylaminobenzil, etc., can be prepared by methods known from the literature (C. Tüzün, M. Ogliaruso and E. I. Becker, Org. Synth. Coll., vol. V, page 111, (1973)).

Numerous of the o-phenyl derivatives are commercially available or can be prepared by methods well known from the literature. For example, 3,4-diaminotoluene, 3,4-diaminoanisole, 3,4-diaminophenetole, 3,4-diamino-o-xylene, 4,5-diamino-o-xylene, or 4,5-diaminoveratrole (cf., p.e., J. Ehrlich and T. M. Bogert, J. Org. Chem., 12, 522 (1947)) can be employed. The quinoxalines according to the invention can be prepared in an ethanolic solution with a hydrogen chloride catalyst or in an acetic acid solution without an additional catalyst. The reaction is performed under reflux conditions and in general is completed within about 3 hours with an almost quantitative yield. The products of an intensive yellow color are isolated by precipitation in water, which optionally has been rendered alkaline. They can be purified by recrystallization from an alcohol/water mixture.

The quinoxalines of the invention, which correspond to the above general formula, unexpectedly show a much greater sensitivity to light than the compounds known from German Pat. No. 1,254,469 (British Pat. No. 1,004,461). It was surprising to find that the interaction of at least two dialkylaminophenyl groups in the 2- and 3-position with at least one electron-donating alkyl group or alkoxyl group in the 5-, 6- or 7-position of the quinoxaline ring is required to achieve high light sensitivity values of the photoconductor.

Quinoxalines of the above general formula, in which $R_1$, $R_2$ and $R_3$ are the same as or different from one another and each denotes hydrogen, methyl, methoxyl or ethoxyl, whereby not more than two of the groups $R_1$, $R_2$ and $R_3$ simultaneously denote hydrogen, methyl, methoxyl or ethoxyl, have been found to be particularly advantageous.

Moreover, it was surprising to find that other parameters of the quinoxalines according to the invention, which are important for the electrophotographic process and for the printing and copying behavior, are not adversely affected, but, on the contrary, are capable of satisfying high demands.

For example, photoconductive layers containing quinoxaline derivatives which correspond to the general formula exhibit only a very low decrease in potential when, after being charged, they are stored in the dark. This is surprising, because for many photoconductive substances it is known that an overloading of a molecule with electrophotographically active substituents, such as, for example, dialkylamino groups or similar electron-donating substituents, often results in a high discharge in the dark.

At the same time, a quick and very complete discharge takes place upon exposure of the electrophotographic recording material of this invention, so that an extraordinarily high potential difference is created between the exposed and unexposed layer portions. After development with a fine-particulate toner substance, perfect, crisp reproductions of high resolution are obtained of the original, and even the finest image elements are exactly reproduced.

Due to the excellent properties exhibited by the quinoxalines according to the present invention and the recording materials in which they are contained, other interesting fields of application are processes where liquid developers are used or, if an appropriate sensitization is performed, laser irradiation.

Further advantageous properties of the recording materials in which the quinoxaline derivatives of the general formula are contained are, for example, their rapid chargeability, high charging capacity and excellent compatibility with polymers of the most diverse compositions whereby, due to their low tendency to crystallize, the quinoxalines of this invention can be used in amounts of up to 95%, if required, without any tendency for crystallization being observed.

The quinoxalines according to the invention also exhibit good compatibility with other organic and inorganic types of photoconductors, so that it is not only possible to use mixtures of several of these quinoxalines, but also mixtures of quinoxalines with other compounds, some of which possess excellent electrophotographic properties.

Electrophotographic recording materials, in which the quinoxalines according to the present invention are contained, can be charged both positively and negatively. Finally, toxicological tests have shown that the quinoxalines according to this invention are physiologically unobjectionable, which is of particular importance in view of environmental nuisance.

The quinoxalines of the invention are readily soluble in customary solvents. Therefore the photoconductors do not impose any special restrictions with regard to the solvents that can be employed for the coating solution or to the chemicals used in the subsequent processing. Thus, these substances can substantially be selected in view of their environmental safety.

Although the quinoxalines according to this invention have film-forming properties, it is nevertheless expedient to mix them with organic polymers in order to obtain a mechanically resistant recording material.

The choice of an appropriate binder is not only determined by its film-forming properties, but also by other properties, such as solubility in alkaline media, electrical behavior and adhesion to the electrically conductive layer support, number of prints which can be run, and, finally, physiological safety. Binders which are soluble in an aqueous or alcoholic solvent with an admixture of an acid or, preferably, alkali, are especially suitable.

High-molecular weight binders of an adequate solubility in alkaline media are advantageously employed. Solubility in alkaline media is achieved by incorporating certain groups, such as, for example, acid anhydride groups, carboxyl groups, phenolic and aliphatic hydroxy groups, sulfonic acid groups, sulfonamide groups or sulfonimide groups or by urethane groups which have been activated by electron-attracting groups.

Copolymers comprising acid anhydride groups, partially esterified acid anhydride groups, carboxyl groups and phenol resins are particularly well suited for producing light-sensitive layers for printing applications, since in mixtures of this type excellent electrophotographic properties and very good printing properties are combined.

Examples of particularly suitable polymers are: copolymers of styrene or substituted styrenes with maleic acid anhydride, copolymers of styrene or substituted styrene with partially esterified maleic acid anhydride, copolymers of acrylic acid, methacrylic acid and acrylic acid esters, and reaction products of polyvinyl acetals containing free hydroxyl groups and sulfonylisocyanates.

If phenolic resins are used as binders, homo- or copolymers of hydroxystyrene or novolak resins are preferred; the latter can, for example, be prepared by condensing phenol or cresol with formaldehyde.

Due to the film-forming properties of the quinoxalines of this invention, the amount of binder can be varied within wide limits, without crystallization or exudation of the photoconductive substance being observed. Embodiments where the ratio of polymer to photoconductor varies between 1:20 and 4:1 are preferred. The best results are achieved when the ratio is between 1:2 and 2:1. The amount of photoconductor thus varies between 20 and 95 percent by weight, relative to the weight of the photoconductive layer.

Although the electrophotographic recording material of this invention is photoconductive per se, its sensitivity to visible light, in particular in spectral ranges of special interest, can be considerably increased by adding sensitizing dyestuffs.

Examples of suitable sensitizing dyestuffs are triphenylmethane dyestuffs, such as Malachite Green (C.I. 42,000), Brillant Green (C.I. 42,040), Crystal Violet (C.I. 42,555) and the like; thiazine dyestuffs, such as Methylene Blue (C.I. 52,015), Methylene Green (C.I. 52,020) and the like; oxazine dyestuffs, such as Capryl Blue (C.I. 48,035) and the like; Astrazon dyestuffs, such as Astrazon Yellow 3GL (C.I. 48,035), Astrazon Orange R (C.I. 48,040), Astrazon Red (C.I. 48,020) and the like; cyanine dyestuffs, such as Aizen Astra Phloxin FF (C.I. 48,070) and the like; xanthene dyestuffs, such as Rhodamin FB (C.I. 45,170) and the like; and pyrylium or benzopyrylium dyestuffs, as well as suitable combinations of these dyestuffs.

Furthermore, indigoide dyestuffs, quinacridone dyestuffs and azo dyestuffs which are soluble in these matrices can be used.

Particularly preferred sensitizing dyestuffs are Astrazon Orange R (C.I. 48,040), Rhodamin FB (C.I. 45,170) and Brillant Green (C.I. 42,040), which may be used alone or as mixtures.

The quantity of sensitizing dyestuff which can be added to the photoconductive layer can be varied from about 0.01 to 30%. Preference is given to an amount of between 1 and 5%, relative to the weight of the photoconductor employed.

Suitable supports for the electrophotographic recording material of this invention are electrically conductive films or metal sheets with hydrophilic surfaces, such as electrically conductive paper, foils and sheets of aluminum or zinc, multimetal sheets, such as copper-/aluminum sheets, chrome/copper sheets and the like or plastic films, which have been metallized or provided with a metal coating by vapor deposition.

Particularly preferred layer supports are sheets or foils of aluminum, which have been appropriately pretreated for rendering their surfaces hydrophilic.

For this purpose, the bright-rolled aluminum sheet is superficially roughened by mechanical brushing or by electrochemical means, optionally etched in an alkaline or acid medium, anodically oxidized in a suitable acid and finally rendered hydrophilic by treatment with a silicate or polyvinylphosphonic acid. These treatment steps not only render the surface of the layer support hydrophilic, but also prevent the occurrence of undesired, deleterious reactions with the electrophotographic layer to be produced on the surface of the support.

If desired, an intermediate layer can be applied between the surface of the layer support and the photoconductive layer, for example, for improving the adhesion of the photoconductive material. It is also possible to coat the photoconductive layer with a top layer which is dissolved away in the decoating step and by which the electrostatic properties of the photoconductive layer are optionally improved and the layer itself is protected from mechanical attack.

The electrophotographic recording layer is prepared by dissolving the binder, the photoconductor, the sensitizers and other additives in a suitable solvent or solvent mixture. The homogeneous solution thus obtained is applied to the layer support and dried. The weight of the dried layer is between 1 $g/m^2$ and 200 $g/m^2$, preferably between 2 $g/m^2$ and 15 $g/m^2$.

Solvents which are suitable for preparing a homogeneous solution of the above-described components include alcohols, ketones, ether alcohols, ethers and esters. At standard pressure, the boiling points of the solvents employed preferably are below 150° C., and the solvent should be physiologically unobjectionable.

If the electrophotographic recording material according to this invention is employed to produce lithographic printing forms, the coated aluminum foil is charged by means of a corona discharge and exposed, for example by means of a screen exposure, contact exposure or laser exposure. Then the latent image formed on the layer is treated with a finely particulate toner, the resulting toner image is fixed and by the subsequent decoating step, in which the toner-free layer portions are removed, the printing original is obtained.

Those areas of the printing original where the surface of the layer support has been laid bare are hydrophilic, whereas those areas of the printing original where toner adheres to the light-sensitive layer are oleophilic. Thus, the printing original is ready for printing. Printed circuits are produced by an analogous process.

The electrophotographic recording material of this invention can be modified by adding appropriate admixtures, such as quinonediazide compounds, which after an overall exposure following the formation of the toner image enhance an improved solubility of the non-image areas.

Other customary additives which may be contained in the photoconductive layer are leveling agents, plasticizers or adhesion promotors.

The electrophotographic recording material prepared in accordance with this invention is preferably employed for the manufacture of printing plates of high sensitivity to light, good resolution and ink reception, and long print runs. The recording material of the invention is also well suited for the production of etch resists.

The invention will be explained in greater detail by the following, non-limiting examples. Of the tables of formulas, which are attached to the specification, Table 1 shows the preferred compounds (I to IV) of the quinoxalines of this invention, which are compared with some of the quinoxalines (V to VIII) mentioned in the cited prior art publications (German Pat. No. 1,254,469, British Pat. No. 1,004,461), which are shown in Table 2. The compounds are characterized by the following data:

| Compound acc. to formula | Melting point (°C.) | | Results of analysis (in %) | | | |
|---|---|---|---|---|---|---|
| | | | C | H | N | Cl |
| I | 142–143.5 | calculated: | 79.4 | 7.8 | 12.8 | |
| | | found: | 79.7 | 7.8 | 12.8 | |
| II | 163–164 | calculated: | 78.5 | 6.9 | 14.7 | |
| | | found: | 78.4 | 6.9 | 14.7 | |
| III | 112–113 | calculated: | 76.9 | 7.7 | 11.9 | |
| | | found: | 77.1 | 7.8 | 12.0 | |
| IV | 196–197 | calculated: | 78.7 | 7.1 | 14.2 | |
| | | found: | 78.8 | 7.0 | 14.1 | |
| V | 185–186 | calculated: | 73.4 | 5.0 | 11.7 | 9.9 |
| | | found: | 73.8 | 5.1 | 11.5 | 9.6 |
| VI | 185–189 | calculated: | 77.7 | 5.9 | 11.8 | |
| (isomeric mixture) | | found: | 77.4 | 5.9 | 11.8 | |
| VII | 123 | calculated: | 81.2 | 5.9 | 12.9 | |
| | | found: | 81.0 | 5.9 | 12.7 | |
| VIII | 140–155 | calculated: | 81.4 | 6.2 | 12.4 | |
| (isomeric mixture) | | found: | 81.1 | 6.4 | 12.6 | |

EXAMPLE 1

By means of a doctor blade, a 0.3 mm thick aluminum foil which had been electrochemically roughened and post-treated with polyvinylphosphonic acid was coated with a coating solution of 30.0 g of a copolymer of styrene and maleic acid anhydride, having a mean molecular weight of 80,000,
23.0 g of 2,3-bis(4'-diethylaminophenyl)-6-ethoxy quinoxaline (compound III),
0.1 g of Rhodamin FB (C.I. 45,170, and
0.6 g of Astrazon Orange R (C.I. 48,040), in
220.0 g of tetrahydrofuran,
140.0 g of ethylene glycol monomethyl ether and
44.0 g of butyl acetate,
in such a way that after evaporation of the solvent mixture a photoconductive layer having a weight of 5.2 g/m² was obtained.

With the aid of a corona, the layer was charged to −450 V and exposed for 14 seconds in a reprographic camera by means of 10 halogen lamps of 600 W each. The original used was a mounting flat containing the usual test elements.

The latent charge image produced by the exposure was developed with a commercially available dry toner and thermally fixed. A clean, crisp image of the original, which was free from tone, was obtained.

To produce the printing form, the aluminum foil which carried the fixed toner image on its photoconductor layer was immersed into a vessel containing a decoating solution. The decoating solution was obtained by dissolving 50 g of sodium silicate in 250 g of glycerol (86%) and deluting the solution with 390 g of ethylene glycol and 310 g of methanol.

Several ten thousands of perfect prints could be run with the developed printing plate in a sheet-fed offset press.

EXAMPLE 2

An electrophotographic recording material prepared as described in Example 1 was tested in a Dyntest apparatus. The incandescent filament lamp used in this apparatus had a temperature of 2,800° K. The layer was charged to −500 V and the discharge in the dark was recorded. After 1 minute the residual potential $U_D$ was −402 V = 80.4%.

If the layer was charged to −500 V and exposed, the residual potential $U_H$ measured after 1 minute was −3 V = 0.6%. After 12 seconds, a discharge to $E_{1/10}$ = −50 V was stated. The half-value sensitivity $E_{\frac{1}{2}}$ was 11.5 µJ/cm².

COMPARATIVE EXAMPLES

In the Examples which follow the layer composition was the same as in Example 1, with the exception that the quinoxaline according to this invention, which was used in Example 1, was replaced by the compounds listed in Table of formulas 2. The resulting layers had weights of between 5.0 g/m² and 5.3 g/m². The layers obtained were tested as described in Example 2.

A. Photoconductor: 2-(4'-dimethylaminophenyl)-3-(4'-chlorophenyl)-quinoxaline (compound V)
Charge: −500 V
Residual potential $U_D$ after 1 minute: −418 V = 83.6%
Residual potential $U_H$ after 1 minute: −85 V = 17.0%
Half-value sensitivity $E_{\frac{1}{2}}$: 33.6 µJ/cm²

B. Photoconductor: 2-(4'-dimethylaminophenyl)-3-phenyl-6-methoxy-quinoxaline (compound VI)
Charge: −500 V
Residual potential $U_D$ after 1 minute: −405 V = 81.0%
Residual potential $U_H$ after 1 minute: −71 V = 14.0%
Half value sensitivity $E_{\frac{1}{2}}$: 30.0 µJ/cm²

C. Photoconductor: 2-(4'-dimethylaminophenyl)-3-phenyl-quinoxaline (compound VII)
Charge: −500 V
Residual potential $U_D$ after 1 minute: −458 V = 91.6%
Residual potential $U_H$ after 1 minute: −68 V = 13.5%
Half-value sensitivity $E_{\frac{1}{2}}$: 26.6 µJ/cm²

D. Photoconductor: 2-(4'-dimethylaminophenyl)-3-phenyl-6-methyl-quinoxaline (compound VIII)
Charge: −500 V
Residual potential $U_D$ after 1 minute: −463 V = 92.5%
Residual potential $U_H$ after 1 minute: −61 V = 12.2%
Half-value sensitivity $E_{\frac{1}{2}}$: 32.6 µJ/cm²

EXAMPLE 3

A coating solution was prepared as described in Example 1, except that the photoconductor of Example 1 was replaced by the compound 2,3-bis(4'-dimethylaminophenyl)-6-methyl quinoxaline (compound II). By means of a doctor blade, the solution was applied to an aluminum foil which had been electrochemically roughened and post-treated with polyvinylphosphonic acid, whereby a dry layer weight of 5.9 g/m² was obtained. The material was tested as described in Example 2.
Charge: −500 V
Residual potential $U_D$ after 1 minute: −445 V = 89.0%
Residual potential $U_H$ after 1 minute: −11 V = 2.2%
Half-value sensitivity $E_{\frac{1}{2}}$: 13.5 µJ/cm²

EXAMPLE 4

The photoconductor of Example 3 was replaced by 2,3-bis-(4'-diethylaminophenyl)-6-methyl quinoxaline (compound I). The dry layer weight was 5.4 g/m² and the test results were the following:
Charge: −500 V Residual potential $U_D$ after 1 minute: $-443$ V$=88.6\%$
Residual potential $U_H$ after 1 minute: $-5$ V$=1.0\%$
Half-value sensitivity $E_{\frac{1}{2}}$: 10.8 $\mu$J/cm$^2$

EXAMPLE 5

A coating solution comprised of
30.0 g of a reaction product of a polyvinyl butyral having a mean molecular weight of 80,000 and containing 71% by weight of vinyl butyral units, 27% by weight of vinyl alcohol units and 2% by weight of vinyl acetate units, and propenylsulfonylisocyanate having an acid number of 158,
23.0 g of 2,3-bis(4'-diethylaminophenyl)-6-methyl quinoxaline (compound I),
0.1 g of Rhodamin FB (C.I. 45,170), and
0.6 g of Astrazon Orange R (C.I. 48,040), in
220.0 g of tetrahydrofuran,
140.0 g of ethylene glycol monomethyl ether and
44.0 g of butyl acetate,
was applied to an aluminum foil as described in Example 1, such that a dry layer weight of 6.0 g/m$^2$ was obtained. The layer was tested as described in Example 2, which led to the following results:
Charge: $-500$ V
Residual potential $U_D$ after 1 minute: $-407$ V$=81.4\%$
Residual potential $U_H$ after 1 minute: $-5$ V$=1.0\%$
Half-value sensitivity $E_{\frac{1}{2}}$: 12.0 $\mu$J/cm$^2$

EXAMPLE 6

A coating solution comprised of
25.0 g of a copolymer of styrene and maleic acid anhydride,
17.5 g of 2,3-bis(4'-diethylaminophenyl)-6-methyl quinoxaline (compound I),
0.4 g of Astrazon Orange R (C.I. 48,040), and
0.2 g of Brillant Green (C.I. 42,040), in
125.0 g of tetrahydrofuran
80.0 g of ethylene glycol monomethyl ether and
25.0 g of butyl acetate
was applied to an aluminum foil which had been electrochemically roughened and post-treated with polyvinylphosphonic acid, such that a dry layer weight of 6.1 g/m$^2$ was obtained.
Tests in accordance with Example 2 gave the following results:
Charge: $-500$ V
Residual potential $U_D$ after 1 minute: $-355$ V$=71.0\%$
Residual potential $U_H$ after 1 minute: $-2$ V$=0.4\%$
Half-value sensitivity $E_{\frac{1}{2}}$: 7.5 $\mu$J/cm$^2$

EXAMPLE 7

The coating composition was the same as in Example 1, except that 42.4 g of the photoconductor (compound III) and 10.6 g of the copolymer were used. The electrophotographic layer obtained had a dry weight of 6.5 g/m$^2$. The photoconductor did not crystallize.
Tests in accordance with Example 2 gave the following results:
Charge: $-500$ V
Residual potential $U_D$ after 1 minute: $-445$ V$=89.0\%$
Residual potential $U_H$ after 1 minute: practically 0
Half-value sensitivity $E_{\frac{1}{2}}$: 8.0 $\mu$J/cm$^2$

EXAMPLE 8

Preparation of 2,3-bis(4'-dimethylaminophenyl)-6,7-dimethyl quinoxaline (compound IV):
14.8 g of 4,4'-bis-dimethylaminobenzil and
7.5 g of 4,5-dimethyl-o-phenylenediamine in 100 ml acetic acid
were heated to the reflux for 3 hours.
The dark-colored solution was allowed to cool down and was then poured into ice water. The mixture was well stirred and the yellow precipitate was removed by suction. After drying, recrystallization from ethanol was performed.
Yield: 18.2 g$=92\%$ of theoretical of needles of intense yellow color.
Melting point: 196° C. to 197° C.

TABLE 1

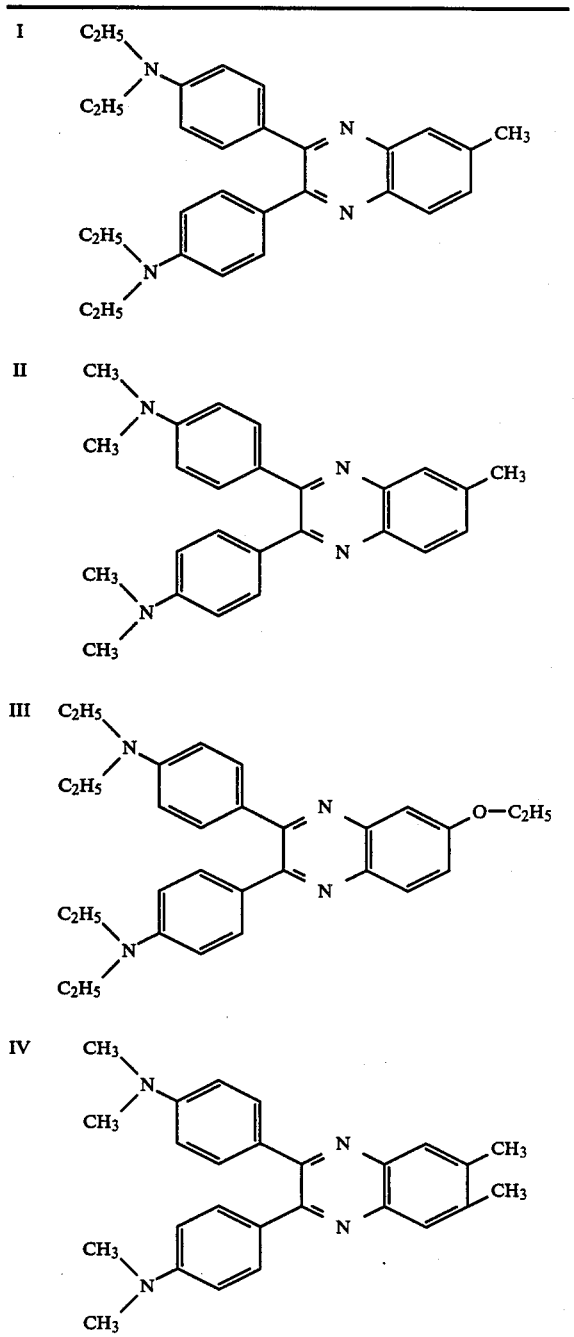

TABLE 2

V
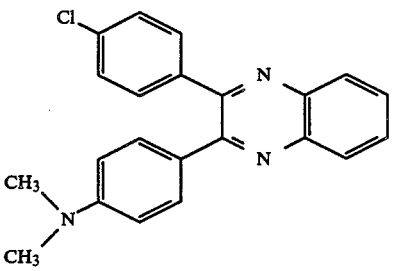

VI
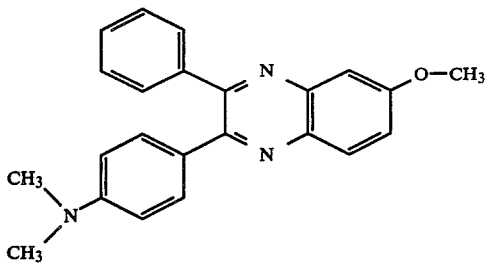

VII
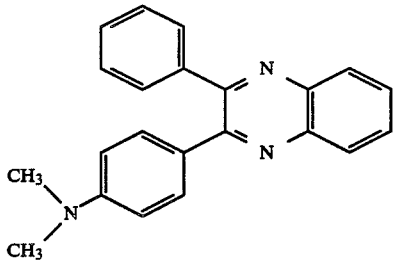

VIII
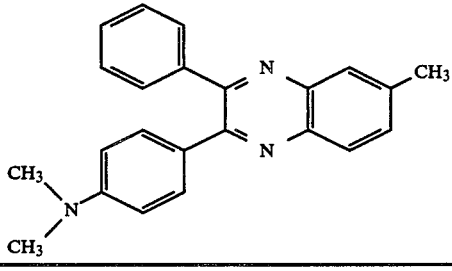

What is claimed is:

1. A 2,3-bis(dialkylaminophenyl)quinoxaline represented by the formula

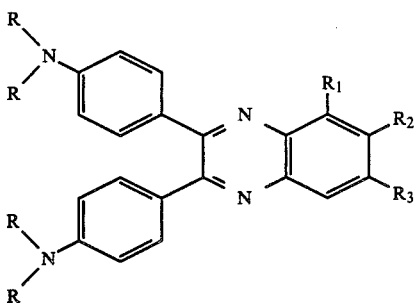

wherein
R is an alkyl having up to 4 carbon atoms,
$R_1$ is hydrogen or alkyl having up to 4 carbon atoms,
$R_2$ is the same as or different from $R_1$ and is selected from the group consisting of alkyl and alkoxyl having up to 4 carbon atoms, and
$R_3$ is the same as or different from $R_2$ and is selected from the group consisting of hydrogen, alkyl and alkoxyl having up to 4 carbon atoms.

2. A quinoxaline as claimed in claim 1, wherein
R is methyl or ethyl
$R_1$ is hydrogen or methyl
$R_2$ is methyl, ethyl, methoxyl or ethoxyl, and
$R_3$ is hydrogen, methyl or methoxyl.

3. A quinoxaline as claimed in claim 1, wherein $R_1$, $R_2$ and $R_3$ are the same or different and are selected from the group consisting of hydrogen, methyl, methoxyl and ethoxyl, wherein not more than two of the groups $R_1$, $R_2$ and $R_3$ simultaneously are hydrogen, methyl, methoxyl or ethoxyl.

4. A quinoxaline as claimed in claim 1, wherein said quinoxaline is 2,3-bis(4'-diethylaminophenyl)-6-methyl quinoxaline, 2,3-bis(4'-dimethylaminophenyl)-6-methyl quinoxaline, 2,3-bis(4'-diethylaminophenyl)-6-ethoxy quinoxaline or 2,3-bis(4'-dimethylaminophenyl)-6,7-dimethyl quinoxaline.

5. An electrophotographic recording material comprising (i) a photoconductive layer comprising a photoconductor, a binder and a sensitizing dyestuff, and (ii) an electrically conductive support to which said layer is provided, wherein said photoconductor is a 2,3-bis(-dialkylaminophenyl)quinoxaline as claimed in claim 1.

6. A recording material as claimed in claim 5, wherein the amount of photoconductor is from about 20 to about 95% by weight of the photoconductive layer.

7. A recording material as claimed in claim 5, wherein said layer further comprises at least one additional organic or inorganic photoconductor.

8. A recording material as claimed in claim 5, wherein said binder is an alkali-soluble binder.

9. A recording material as claimed in claim 8, wherein said binder is comprised of at least one copolymer of styrene or substituted styrene and maleic acid anhydride.

10. A recording material as claimed in claim 5, wherein the dyestuff is at least one of a group consisting of Astrozon Orange, Rhodamin FB and Brilliant Green.

11. A recording material as claimed in claim 5, wherein the electrically conductive support is selected from the group consisting of an aluminum sheet and an aluminum foil, said support having been pretreated to render its surface hydrophilic.

* * * * *